(12) United States Patent
Yamaguchi (10) Patent No.: US 9,348,787 B2
(45) Date of Patent: May 24, 2016

(54) METHOD AND SYSTEM FOR PROCESSING ANALYSIS DATA

(75) Inventor: Shinichi Yamaguchi, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 559 days.

(21) Appl. No.: 13/806,831

(22) PCT Filed: Jul. 6, 2010

(86) PCT No.: PCT/JP2010/061442
§ 371 (c)(1),
(2), (4) Date: Dec. 24, 2012

(87) PCT Pub. No.: WO2012/004855
PCT Pub. Date: Jan. 12, 2012

(65) Prior Publication Data
US 2013/0096847 A1   Apr. 18, 2013

(51) Int. Cl.
*G06F 15/00* (2006.01)
*H01J 49/02* (2006.01)
(Continued)

(52) U.S. Cl.
CPC ............... *G06F 15/00* (2013.01); *G01N 30/86* (2013.01); *G01N 30/8675* (2013.01); *G04F 13/00* (2013.01); *H01J 49/0036* (2013.01); *H01J 49/02* (2013.01)

(58) Field of Classification Search
CPC ... G01N 30/72; G01N 30/86; G01N 30/8655; G01N 30/8675; G01N 33/0004; G04F 13/00; G06F 15/00; G06F 19/24; G06F 19/703; H01J 49/0027; H01J 49/0036; H01J 49/02
USPC .......... 702/22, 23, 27, 176; 250/281; 707/602
See application file for complete search history.

(56) References Cited

U.S. PATENT DOCUMENTS 8,214,323 B2 * 7/2012 Zigon et al. .................. 707/602
2009/0020693 A1   1/2009 Yamaguchi

FOREIGN PATENT DOCUMENTS

| JP | 2007240374 A | 9/2007 |
| JP | 2009025056 A | 2/2009 |
| JP | 2009053070 A | 3/2009 |

OTHER PUBLICATIONS

Yonekubo et al., "Feature of newest Time of Flight Mass Spectrometer LCT Premier(TM) and Applied for Food Metabolome" (with English abstract) Chromatography, vol. 27, No. 2, pp. 85-89, 2006.
(Continued)

*Primary Examiner* — John H Le
(74) *Attorney, Agent, or Firm* — Morgan, Lewis & Bockius LLP (57) ABSTRACT

Data for a plurality of samples collected by an LC/MS, GC/MS or other systems are converted into a two-dimensional table format without losing information and with a light load, thereby allowing a multivariate analysis processing to be efficiently performed. After LC/MS data on a plurality of samples are obtained and the respective extracted ion chromatograms (XICs) are created (S1 and S2), the correction of the retention-time difference, the waveform processing and the like are performed (S3 and S4), followed by the creation of a one-dimensional table in which the signal-strength values are arranged for each XIC. Then, one-dimensional tables of a plurality of XICs for one sample are joined together in order of m/z value to create an elongate one-dimensional table (S5). The elongate one-dimensional tables of a plurality of samples are arranged in another dimensional direction to obtain a two-dimensional table (S6).

8 Claims, 3 Drawing Sheets

(51) Int. Cl.
*G04F 13/00* (2006.01)
*G01N 30/86* (2006.01)
*H01J 49/00* (2006.01)

(56) References Cited

OTHER PUBLICATIONS

Sangster, et al., "Investigation of analytical variation in metabonomic analysis using liquid chromatography/mass spectrometry" Rapid Communications in Mass Spectrometry, vol. 21, pp. 2965-2970, 2007.

Xiayan et al., "Advances in separation science applied to metabonomics" Electrophoresis, vol. 29, pp. 3724-3736, 2008.

Japanese language international search report dated Aug. 3, 2010 and its English language translation issued in corresponding PCT application PCT/JP2010/061442.

Japanese language international preliminary report on patentability dated Feb. 12, 2013 and its English language translation issued in corresponding PCT application PCT/JP2010061442.

\* cited by examiner

Fig. 4A
XIC OF SAMPLE 1 AT m/z100

Fig. 4B

| m/z | TIME | SAMPLE 1 |
|---|---|---|
| 100 | 1.1 | 12 |
|  | 1.2 | 3 |
|  | 1.3 | 111 |
|  | ---- | ---- |

Fig. 4C

| m/z | TIME | SAMPLE 1 |
|---|---|---|
| 100 | 1.1 | 12 |
|  | 1.2 | 3 |
|  | 1.3 | 111 |
|  | ---- | ---- |
| 101 | 1.1 | 360 |
|  | 1.2 | 125 |
|  | 1.3 | 1220 |
|  | ---- | ---- |
| 120 | 1.1 | 3 |
|  | 1.2 | 1 |
|  | 1.3 | 1 |
|  | ---- | ---- |
| 130 | ---- | ---- |
|  | ---- | ---- |

Fig. 4D

| m/z | TIME | SAMPLE 1 | SAMPLE 2 | SAMPLE 3 | ---- |
|---|---|---|---|---|---|
| 100 | 1.1 | 12 | 24 | 20 |  |
|  | 1.2 | 3 | 1 | 0 |  |
|  | 1.3 | 111 | 500 | 240 |  |
|  | ---- | ---- | ---- | ---- |  |
| 101 | 1.1 | 360 | 80 | 30 |  |
|  | 1.2 | 125 | 800 | 90 |  |
|  | 1.3 | 1220 | 8000 | 560 |  |
|  | ---- | ---- | ---- | ---- |  |
| 120 | 1.1 | 3 | 8 | 10 |  |
|  | 1.2 | 1 | 0 | 2 |  |
|  | 1.3 | 1 | 3 | 2 |  |
|  | ---- | ---- | ---- | ---- |  |
| 130 | ---- | ---- | ---- | ---- |  |
|  | ---- | ---- | ---- | ---- |  |

METHOD AND SYSTEM FOR PROCESSING ANALYSIS DATA

TECHNICAL FIELD

The present invention relates to a method and system for processing data collected by an analyzing device. More specifically, it relates to a method and system for processing data collected by an analyzing device in which a separation technique for separating the components of a sample one-dimensionally with time as the separation factor, such as liquid chromatography, gas chromatography or capillary electrophoresis, is combined with a measurement technique for acquiring a signal strength for the sample, where the signal is separated in one or more dimensional directions with an element or elements other than time as the separation factor, such as a mass spectrometry, infrared spectrometry or ultraviolet-visible spectrometry.

BACKGROUND ART

In an analysis such as an LC/MS, GC/MS or CE/MS analysis, in which the liquid chromatography (LC), gas chromatography (GC), capillary electrophoresis (CE) or a similar technique for separating the components of a sample is combined with a mass spectrometry (MS), a large number of components contained in a sample are temporally separated, and a mass spectrometric data is obtained for each component. These techniques make it possible to efficiently analyze a sample in which various kinds of compounds are mixed. Therefore, in recent years, they have been applied to a wide range of fields. However, a problem exists in that the amount of data obtained by the measurement is considerably large. This problem is particularly serious in the case of performing an evaluation in which the results of analyses of a large number of similar samples are compared. Since a large amount of mass spectrometric data is obtained for each sample, the entire amount of data to be processed is so large that a comprehensive analysis is difficult. One conventional technique for dealing with this difficulty is a multivariate analysis, such as a discrimination analysis, principal component analysis or cluster analysis, which are all capable of analyzing a large amount of data in a relatively easy way.

For example, Non-Patent Document 1, Patent Document 1 and other documents disclose a technique in which mass spectrum data obtained for a plurality of samples are processed by a principal component analysis and the results are presented using the charts called the "scores plot" and "loadings plot." Examples of commonly known multipurpose software products for conducting a multivariate analysis of a mass spectrometric data in the previously described manner include SIMCA-P+ produced by Umetrics AB, Sweden, and Pirouette® produced by Infometrix, Inc., USA. These products can be easily obtained. However, for the measurement data to be read and processed by these multivariate analysis software systems, it is necessary to compile the measurement data to be analyzed (e.g. mass spectrum data or chromatogram data in the case of an LC/MS) into a table format, i.e. a set of numerical data arrayed in a one-dimensional or two-dimensional (rows and columns) form.

Conventionally, in an analysis using an infrared spectrometer (IR) or nuclear magnetic resonator (NMR), it is common that the data collected from a large number of samples are processed and evaluated by a multivariate analysis. This is due to the fact that, in the case of the IR or NMR, the data obtained by a measurement on a sample is simpler than those obtained by the LC/MS or GC/MS. The result of an analysis by the IR or NMR is simple and can be presented by one graph, i.e. a one-dimensional numerical data representing the strength of a signal with respect to a certain kind of physical quantity (i.e. the wavelength for IR or the chemical shift for NMR). Accordingly, when the results of the analyses of a plurality of samples must be compared, the entire measurement data can be compiled into a two-dimensional table containing numerical values indicating the signal strengths arranged in two directions, one direction corresponding to the variable showing a sequence number or similar numerical values assigned to each sample and the other direction corresponding to the variable showing the aforementioned physical quantity.

By contrast, the measurement data obtained by an LC/MS, GC/MS or similar system are a collection of signal strengths obtained on two directions corresponding to two independent separation factors, i.e. time and mass-to-charge ratio (m/z). This means that these data themselves are in a two-dimensionally arrayed form. Therefore, when the results of analyses of a plurality of samples must be compared, it is necessary to convert the two-dimensional array of data into a one-dimensional array and then compile the measurement data of the plurality of samples into one table.

One of the simplest methods for converting the two-dimensional array of data having the directions of time and mass-to-charge ratio into a one-dimensional array is to select one specific mass-to-charge ratio from a plurality of mass-to-charge ratios, and another method is to total the signal strengths in the direction of mass-to-charge ratio. Both methods are intended for virtually fixing the variable corresponding to the direction of mass-to-charge ratio to one value, which means removing the dimension corresponding to the direction of mass-to-charge ratio. Selection of one specific mass-to-charge ratio from a plurality of mass-to-charge ratios corresponds to selection of one extracted ion chromatogram (XIC) from LC/MS (or GC/MS) data. Totaling the signal strengths in the direction of mass-to-charge ratio throughout the entire range of mass-to-charge ratios corresponds to obtaining a total ion current chromatogram (TIC) from LC/MS data. These methods have the advantages that an uncertainty depending on internal parameters used in the data processing operation for the conversion into a one-dimensionally arrayed form (as will be described later) is reduced, the process is so simple that it puts only a light load on the hardware system, and the processing time is so short that the throughput is high.

However, in the case of the TIC, the information in the direction of mass-to-charge ratio is entirely lost. In the case of the XIC, although the information of one mass-to-charge ratio is retained, the information on the other mass-to-charge ratios is entirely lost. In any of these cases, it can be said that the obtained result is substantially deficient in the information in the dimension corresponding to the direction of mass-to-charge ratio, Such a loss of information in one of the two dimensions leads to the problem that, if the lost information contains some important information that characterizes the difference among the plurality of samples, no appropriate information for evaluating the similarity or difference of those samples can be obtained by multivariate analyses and the samples cannot be correctly compared.

On the other hand, Non-Patent Documents 2 and 3 disclose a technique in which a collection of data obtained by an LC/MS are subjected to a complex data processing operation, including the steps of peak detection and selection, noise removal and strength calculation, to remove and/or integrate unnecessary data so as to convert a two-dimensional array of data into a one-dimensional form, after which the measurement data obtained for each of the samples are compiled into a two-dimensional table to be subjected to a principal component analysis. Phenomenome Profiler™, a set of software tools for metabolomics analyses provided by Phenomenome Discoveries Inc., Canada, has the function of compiling a collection of data obtained by an LC/MS capable of MS$^n$ analyses into a two-dimensional table format by performing a data conversion process including the steps of peak detection, smoothing, calibration and so on.

However, such a complex data processing operation puts a heavy load on the hardware system, and therefore, requires high-performance CPUs and large-capacity random access memories. It also lowers the throughput of the process. The previously described data processing operation uses previously set operation parameters, and these parameters can cause a significant difference in the result of the multivariate analysis. The peak detection or similar processing causes the loss of the original information during the process, which may possibly prevent the difference of the samples from being correctly reflected in the results of the multivariate analysis. Due to these reasons, in some cases, it is impossible to correctly compare the samples despite the complicated data processing.

BACKGROUND ART DOCUMENT

Patent Document

Patent Document 1: JP-A 2009-25056

Non-Patent Document

Non-Patent Document 1: Jun Yonekubo et al., "Feature of newest Time of Flight Mass Spectrometer LCT Premier™ and Applied for Food Metabolome", *Chromatography*, The Society for Chromatographic Sciences, Vol. 27, No. 2 (2006)

Non-Patent Document 2: Tim P. Sangster et al., "Investigation of analytical variation in metabonomic analysis using liquid chromatography/mass spectrometry", *Rapid Commun. Mass Spectrom.*, Vol. 21, pp. 2965-2970 (2007)

Non-Patent Document 3: Li Xiayan et al., "Advances in separation science applied to metabonomics", *Electrophoresis*, Vol. 29, pp. 3724-3736 (2008)

SUMMARY OF THE INVENTION

Problem to be Solved by the Invention

The present invention has been developed in view of the previously described problems, and its primary objective is to provide an analysis data processing method and system capable of effectively using information held in the measurement data obtained for a number of samples by an LC/MS, GC/MS or similar analyzing device and performing a comprehensive analysis to correctly compare those samples, i.e. to obtain correct information relating to the similarity, difference or other aspects of the samples.

Means for Solving the Problems

The first aspect of the present invention aimed at solving the previously described problems is an analysis data processing method for processing signal-strength data collected for each of a plurality of samples under two or more dimensional separation factors, the data being collected by using an analyzing device having: a separator section for separating a plurality of components in a sample along a one-dimensional direction with time serving as the separation factor; and an analyzer section for acquiring, for a sample separated into components by the separator section in the direction of time, a signal strength in a separated form in one or more dimensional directions corresponding to one or more separation factors other than time, and the method including:

a) a first processing step, in which a process is performed to create a one-dimensional table in which, while a second variable based on the separation factor in the separator section is varied under the condition that a first variable based on the separation factor in the analyzer section is fixed, signal-strength values are arranged in an array direction of the numerical values of the second variable, and this process is repeated, while changing the first variable, to create a plurality of one-dimensional tables for each of the plurality of samples;

b) a second processing step, in which the plurality of one-dimensional tables created for the same sample in the first processing step are joined in the array direction of the numerical values of the second variable to create, for each of the plurality of samples, a one-dimensional table consisting of a series of signal-strength values associated with the same value of the first variable; and c) a third processing step, in which the one-dimensional tables respectively created for different samples in the second processing step are arranged in a direction orthogonal to the dimension of the one-dimensional tables to create a two-dimensional table.

The second aspect of the present invention aimed at solving the previously described problems is a data processing system for carrying out the analysis data processing method according to the first aspect of the present invention. This system is an analysis data processing system for processing signal-strength data collected for each of a plurality of samples under two or more dimensional separation factors, the data being collected by using an analyzing device having: a separator section for separating a plurality of components in a sample along a one-dimensional direction with time serving as the separation factor; and an analyzer section for acquiring, for a sample separated into components by the separator section in the direction of time, a signal strength in a separated form in one or more dimensional directions corresponding to one or more separation factors other than time, and the system including:

a) a first processing section, in which a process is performed to create a one-dimensional table in which, while a second variable based on the separation factor in the separator section is varied under the condition that a first variable based on the separation factor in the analyzer section is fixed, signal-strength values are arranged in an array direction of the numerical values of the second variable, and this process is repeated, while changing the first variable, to create a plurality of one-dimensional tables for each of the plurality of samples;

b) a second processing section, in which the plurality of one-dimensional tables created for the same sample in the first processing section are joined in the array direction of the numerical values of the second variable to create, for each of the plurality of samples, a one-dimensional table consisting of a series of signal-strength values associated with the same value of the first variable; and c) a third processing section, in which the one-dimensional tables respectively created for different samples in the second processing section are arranged in a direction orthogonal to the dimension of the one-dimensional tables to create a two-dimensional table.

For example, the separator section in the first or second aspect of the present invention is a liquid chromatograph, gas chromatograph or capillary electrophoresis system, and the separation factor in the separator section is time. Accordingly, the "signal-strength values obtained by varying, under the condition that a first variable based on the separation factor in the analyzer section is fixed, a second variable based on the separation factor in the separator section" is, in the broad sense, a chromatogram in which the strength of a signal varies with time.

On the other hand, the analyzer section is not limited to any specific type but may be any device that can acquire a signal strength separated in one or more directional dimensions corresponding to one or more separation factors other than time. A typical example of the analyzer section is a mass spectrometer in which the mass-to-charge ratio serves as a separation factor. Other examples include ultraviolet-visible spectrophotometers, photodiode array spectrophotometers and infrared spectrometers, in which the wavelength serves as a separation factor, as well as nuclear magnetic resonance apparatuses, in which the chemical shift serves as a separation factor.

The first variable does not need to be the value itself of the separation factor. For example, in the case where the analyzer section is a mass spectrometer, although the first variable may be the value itself of the mass-to-charge ratio, it is also possible to use, as the first variable, a value obtained by performing various conversions or processes that retain information relating to the separation factor concerned, such as an addition or subtraction of a plurality of mass-to-charge ratios or mass-to-charge ratio ranges, or a combination of these operations. When the first variable is the value itself of the mass-to-charge ratio, the aforementioned "chromatogram in the broad sense" is an extracted ion chromatogram. Furthermore, it is also possible to add a total ion chromatogram and/or include a base peak chromatogram, mass defect chromatogram, isotopic filtered chromatogram, neutral-loss chromatogram or other kinds of chromatograms.

For example, in the case where the analyzer section is an LC/MS, signal-strength values corresponding to the two separation factors of mass-to-charge ratio and time (retention time) are obtained as the measurement data. The mass-to-charge ratio is a physical quantity possessed by an ion originating from a substance (compound) contained in a sample. Therefore, this information is inherent in that substance and depends on neither the analyzing environment (e.g. the type of used system) nor analyzing conditions. On the other hand, the time changes depending on the environment and/or conditions of the analysis. If the analysis is made under the same environment and conditions, the time depends solely on the kind of substance and can be used for comparing different samples. However, this information is not an inherent property of the substance.

In the analysis data processing method according to the first aspect of the present invention, in the first processing step, a temporal change in the signal-strength value obtained at a specific value of a kind of information inherent in the substance (e.g. the mass-to-charge ratio), i.e. a chromatogram data such as an extracted ion chromatogram, is acquired for one sample, and the signal-strength values are sequentially arranged in the array direction of the time values to create a one-dimensional table. Such a one-dimensional table is created for each of the mass-to-charge ratios in question. Such a process of creating a one-dimensional table having signal-intensity values arrayed according to the lapse time is similarly performed for each of a plurality of samples. In the second processing step, a plurality of one-dimensional tables related to the same sample are joined in the array direction of the time values to create an elongate table. In the third processing step, the one-dimensional tables respectively created for different samples to be compared are arranged in another dimensional direction to create a two-dimensional table.

Effect of the Invention

In the case where the analyzer section is an LC/MS or GC/MS, the mass spectrum data and chromatogram data related to a plurality of samples are converted into a two-dimensional table format by the previously described process. The numerical values held in this two-dimensional table can be put into a multivariate-analysis software program to perform a data processing for obtaining a comprehensive analysis result which reflects both the information in the direction of time and the information in the direction of mass-to-charge ratio. It is naturally possible to incorporate into the present invention the function realized by a commonly known multivariate-analysis software program to continuously perform the processes from the conversion of data into the two-dimensional table to the multivariate analysis processing. That is to say, the analysis data processing method according to the first aspect of the present invention may preferably include a multivariate analysis step in which numerical values held in the two-dimensional table created in the third processing step are read and subjected to a multivariate analysis.

In the analysis data processing method and system according to the present invention, no complex data processing, such as the peak detection, is required in the process of reflecting numerical data in the tables. Therefore, no inappropriate rounding, emphasizing or other operations due to the internal parameters used in the data processing operation is performed on the information. This makes it possible to more accurately and correctly evaluate the similarity or difference among a plurality of samples.

For example, in the two-dimensional table created in the previously described manner, the data (signal-strength values) held in one vertical column are the data originating from the same sample, while the data (signal-strength values) held in one horizontal row are the data originating from each sample at either a specific mass-to-charge ratio or a value based on a plurality of mass-to-charge ratios and at a specific retention time. In this table, the chromatogram data constituting one chromatogram are arranged in a vertically packed form (i.e. in adjacent cells), while the chromatogram data which are included in the chromatograms and related to the same mass-to-charge ratio or the same value based on a plurality of mass-to-charge ratios in different samples are arranged in a horizontally packed form. It is common that a judgment on the identity of components contained in different samples is made by comparing the shapes of the peak patterns of chromatograms related to the same mass-to-charge ratio or the same value based on a plurality of mass-to-charge ratios. The previously described arrangement of the data has an additional advantage in that analysis operators can easily grasp the shape of the peak pattern of each chromatogram from the signal-strength values held in the table and intuitively compare the shapes of the peak patterns of a plurality of samples.

As the data values, i.e. the signal-strength values, the values obtained by the analyzer section may be directly used. However, this may possibly result in too strong an influence of the absolute strengths on the result of the multivariate analysis to correctly perform a comparative evaluation. To address this problem, a simple data processing for alleviating the difference in the strength values on the chromatogram for the same value of the first variable among different samples may be performed. One example of such a data processing is the normalization of the strength values on the same chromatogram by using the maximum value, variance or standard deviation of the strength.

BEST MODE FOR CARRYING OUT THE INVENTION

Figure 1:
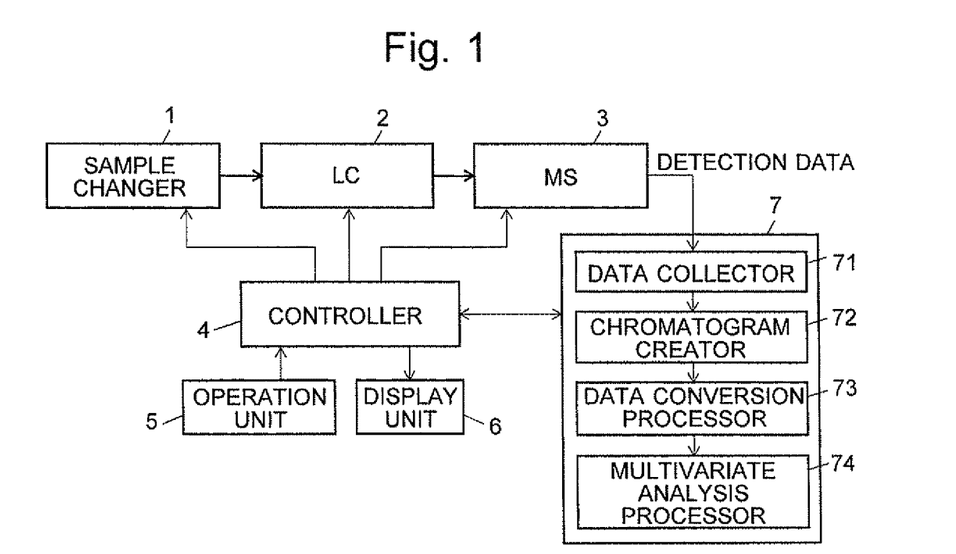
FIG. 1 is a schematic block diagram showing the configuration of one embodiment of an LC-MS analyzer system having an analysis data processing system according to the present invention.

One mode of the analysis data processing method according to the present invention and the analysis data processing system in which the aforementioned method is carried out are hereinafter described, taking as an example an LC-MS analyzer system including the aforementioned analysis data processing system. FIG. 1 is a schematic block diagram showing the configuration of this LC-MS analyzer system.

In FIG. 1, under the control of a controller 4, a sample changer 1 sequentially selects a plurality of prepared samples and introduces it into a liquid chromatograph (LC) unit 2. The LC unit 2, which includes a column for separation, receives the sample from the sample changer 1 and introduces it into the column. While passing through this column, the sample is temporally separated into various kinds of components, which are then sequentially sent to a mass spectrometer (MS) unit 3.

Though not shown, the MS unit 3 is, for example, an ion-trap time-of-flight mass spectrometer (IT-TOFMS) including an atmospheric pressure ion source such as an electrospray ion source, an ion trap, a time-of-flight mass spectrometer and an ion detector. In this MS unit 3, the sample components in an eluate introduced from the LC unit 2 are ionized, and the thereby produced ions are temporarily held in the ion trap. The held ions are given a certain amount of kinetic energy in this ion trap, to be sent into the time-of-flight mass spectrometer. While flying in the flight space, the ions are separated according to their mass-to-charge ratios, to be sequentially detected at the ion detector.

The detection signal obtained in the MS unit 3 is sent to a data processor 7, in which they are converted into digital data and entirely stored in a data collector 71 including a data memory. Subsequently, under the command of the controller 4, a chromatogram creator 72 reads predetermined data from the data collector 71 and creates various kinds of chromatograms, such as an extracted ion chromatogram (hereinafter abbreviated as "XIC"). The created chromatograms are processed by a data conversion processor 73, whereby mass spectrum data and chromatogram data obtained for a plurality of samples are compiled into one table (a two-dimensional array of data). This table is displayed on the screen of a display unit 6 via the controller 4. The same table is also input to a multivariate analysis processor 74, which performs a data processing, such as a principal component analysis, to obtain a multivariate analysis result, such as the scores plot. This result is also displayed on the screen of the display unit 6 via the controller 4.

The controller 4 not only controls the operations of the sample changer 1, LC unit 2, MS unit 3 and data processor 7, but also receives user operations and shows analyzed results, such as the aforementioned scores plot, through an operation unit 5 and display unit 6, both units serving as a user interface. Most of the functions of the controller 4 and data processor 7 can be embodied by means of a personal computer having a predetermined controlling and processing software program installed thereon. As for the functions of the multivariate analyzer 74, a general-purpose multivariate software product can be used, such as the aforementioned SIMCA-P+.

In the LC-MS system of the present embodiment, the samples to be analyzed are similar to each other and contain almost the same components. The kinds of components contained are basically known beforehand. Since the mass-to-charge ratio is inherent in each substance and unaffected by the analyzing conditions and other factors, knowing the kinds of components contained means knowing the mass-to-charge ratios to be monitored. Accordingly, the analysis operator, using the operation unit 5, inputs beforehand a plurality of mass-to-charge ratios to be monitored as one item of the measurement conditions, and then enters a command for executing the measurement. In the present example, it is assumed that m/z 100, 101, 120, 130 and so on have been set as the mass-to-charge ratios to be monitored. According to this condition, the MS unit 3, under the control of the controller 4, repeatedly performs a selective ion monitoring (SIM) measurement for m/z 100, 101, 120, 130 and so on.

Figure 3:
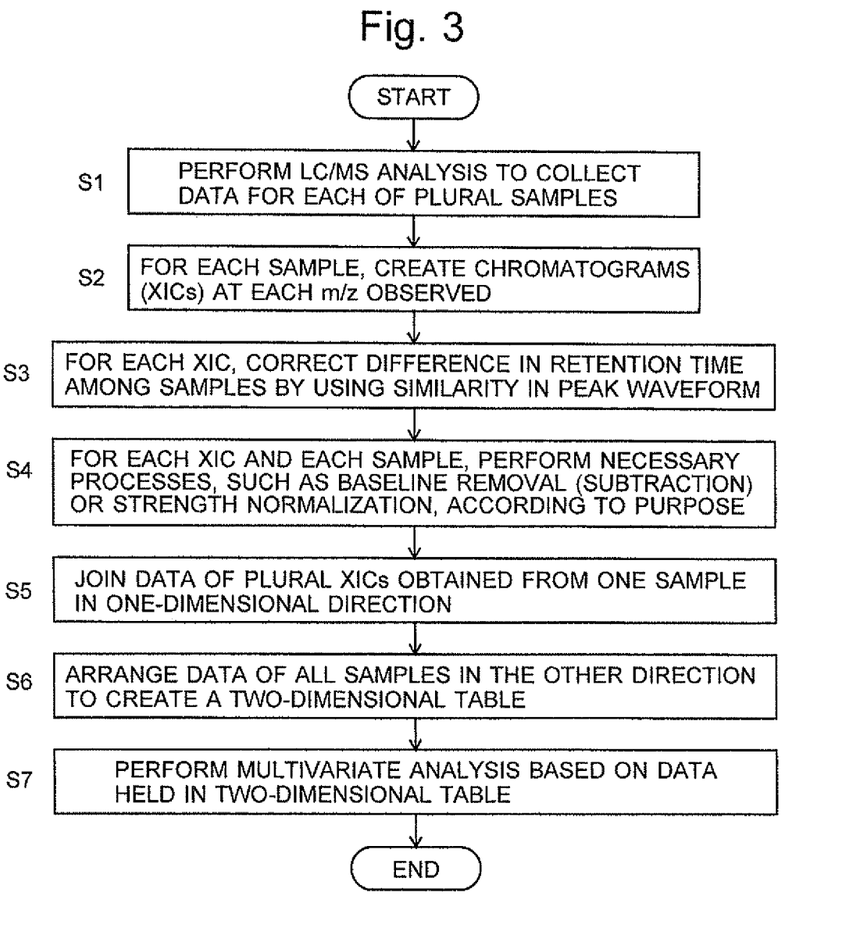
FIG. 3 is a flowchart showing the procedure of a data processing which is characteristic of the LC-MS analyzer system of the present embodiment.

When the measurement is initiated, the sample changer 1 selects one of the samples in a specified order and sends it into the LC unit 2. The LC unit 2 temporally separates the components in the sample, while the MS unit 3 repeatedly performs the SIM measurement for the mass-to-charge ratios that have been set in the aforementioned manner. After the LC/MS measurement for one sample has been completed, the sample changer 1 selects the next sample and sends it into the LC unit 2. The LC unit 2 and the MS unit 3 once again perform the measurements in the previously described manner. Thus, the LC/MS measurement is performed for all the samples. The data collector 71 temporarily holds the thereby obtained data (Step S1).

Figure 2:
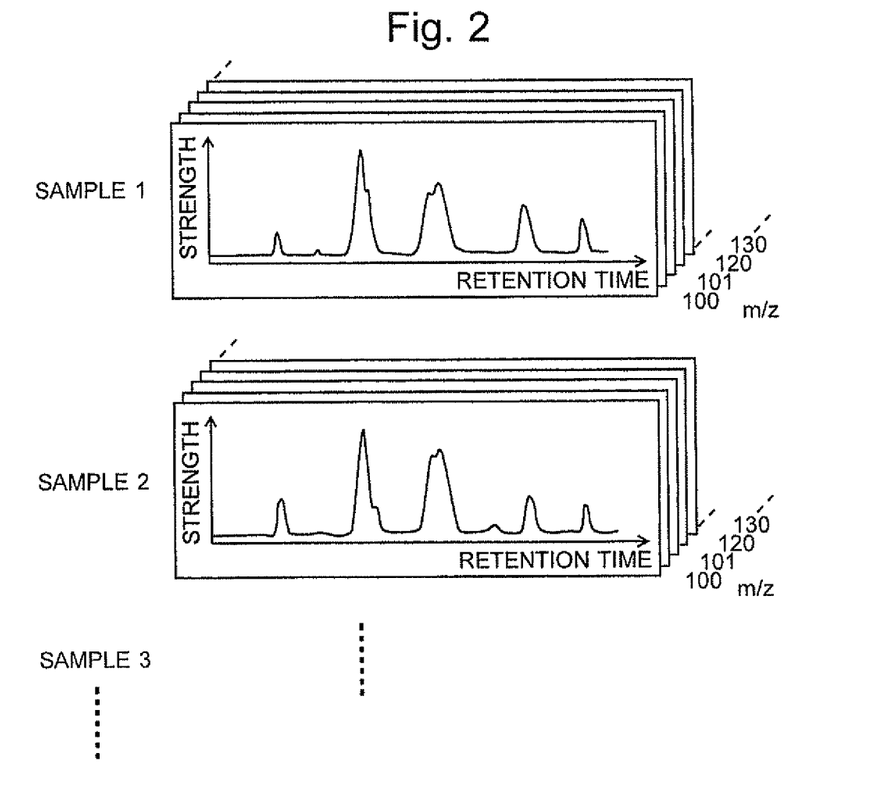
FIG. 2 is an explanatory diagram of chromatogram data collected in the LC-MS analyzer system of the present embodiment.

Next, the chromatogram creator 72 creates, for each sample, an XIC for each of the monitored mass-to-charge ratios (Step S2). For example, if the number of monitored mass-to-charge ratios is eight, there will be eight XICs created per one sample (see FIG. 2). Furthermore, the chromatogram creator 72 compares the peak waveforms of the XICs obtained at the same mass-to-charge ratio of different samples, and based on their similarity, identifies a peak originating from the same component. Then, it calculates the time differences between the peaks originating from the same component, i.e. the differences in the retention time between the samples, and corrects the XICs to cancel those differences (Step S3). These differences in the retention time result from the variation in the flow velocity of the mobile phase in the LC unit 2, the variation in the temperature of the column, or the variation of any other factor that affects the component separation characteristics.

Subsequently, for the XICs of each sample, a waveform processing is performed according to the purpose of the measurement or other factors. For example, this processing may include the determination and removal of the baseline of the XICs, or the normalization of the signal strengths on the XICs (Step S4). In the case of normalization, for example, the maximum value, variance or standard deviation of the signal strengths on each XIC can be used as the basis for normalizing each of the signal-strength values.

Subsequently, the data conversion processor 73 compiles the XIC data of the samples into a two-dimensional table format. Specifically, this process is performed by the following procedure.

Figure 4A:
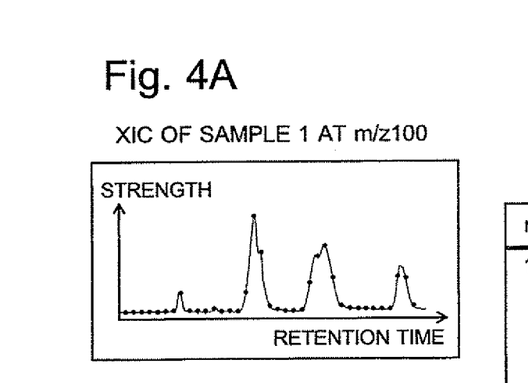
FIGS. 4A-4D are model diagrams showing a specific example of the data processing shown in FIG. 3.
Figure 4B:
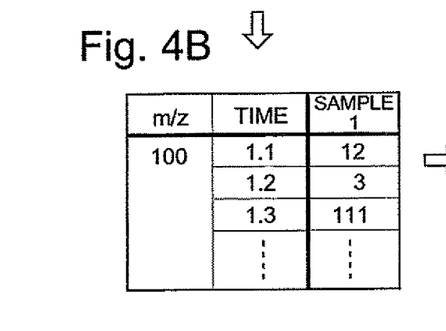

The data which constitute an XIC for one mass-to-charge ratio in one sample, as shown in FIG. 4A, are data each of which indicates the signal-strength value at each point in time (retention time) on the time axis. Taking this into account, a one-dimensional table in which the signal-strength values are arrayed in a one-dimensional direction with respect to the change in time is created for each XIC in one sample. FIG. 4B is one example of the one-dimensional table created for an XIC obtained at m/z 100.

Figure 4C:
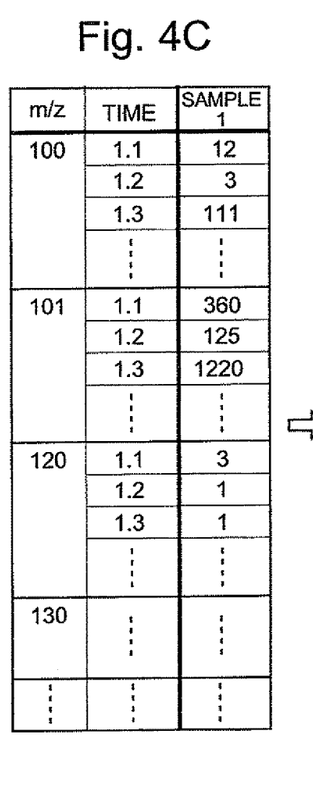

Similar one-dimensional tables are also created for the other mass-to-charge ratios (m/z 101, 120, 130, and so on). These one-dimensional tables are joined in the increasing (or decreasing) order of mass-to-charge ratio in the array direction of the signal-strength values held in the tables (Step S5). FIG. 4C is one example created by joining one-dimensional tables for different mass-to-charge ratios in Sample 1. In the one-dimensional direction of the obtained table (the vertical direction in FIG. 4C), the signal-strength values are not grouped by the retention time, which is a type of information that can be affected by the measurement conditions or other factors, but by the mass-to-charge ratio, which is a type of information inherent in the substance.

Figure 4D:
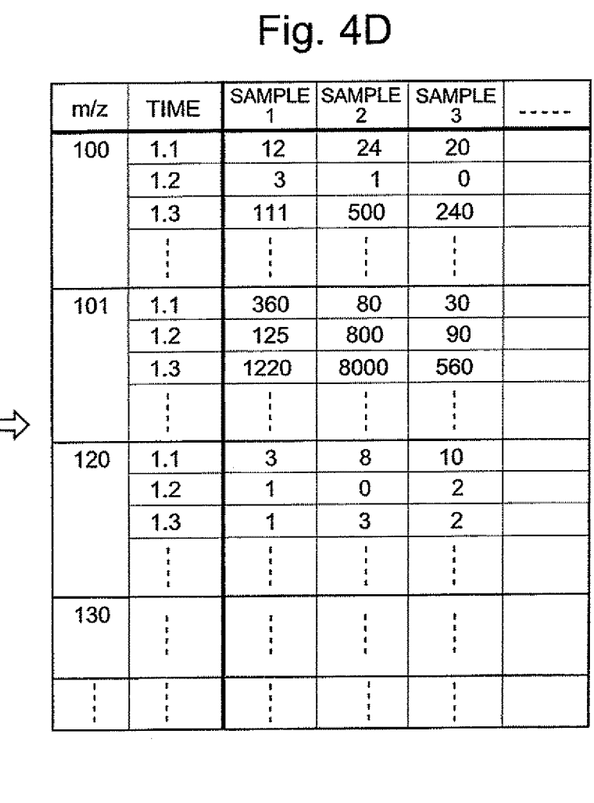

Similarly, a one-dimensional table in which signal-strength values constituting a plurality of XICs are arrayed in a one-dimensional direction is created for each of the samples. Then, the one-dimensional tables created for all the samples are arranged in the other dimensional direction in order of the number assigned to each sample, so as to combine them into a two-dimensional table format as shown in FIG. 4D. That is to say, in the two-dimensional table shown in FIG. 4D, each vertical column holds signal-strength data of all the XICs in one sample. In each column, the signal-strength values for the same mass-to-charge ratio are adjacently held in a packed form. On the other hand, each horizontal row holds signal-strength data of all the samples obtained at one mass-to-charge ratio and at one point in time.

The signal-strength data compiled into the previously described two-dimensional table format by the data conversion processor 73 are sent to the multivariate analysis processor 74. The multivariate analysis processor 74 performs a predetermined type of multivariate analysis processing to obtain a result demonstrating the similarity or difference of the samples, and shows the result on the display unit 6 (Step S7). In the case where the multivariate analysis processor 74 performs a principal component analysis, the scores and loadings are computed for each sample on the basis of the read signal-strength data, and the respective dispersion diagrams are created and displayed. With these diagrams, the analysis operator can evaluate the similarity or difference of a plurality of samples.

In the previously described embodiment, the chromatogram data shown in FIG. 4B are signal-strength data of an XIC for one mass-to-charge ratio, and a one-dimensional table as shown in FIG. 4C is created by using signal-strength data of XICs for a number of mass-to-charge ratios. However, a portion or all of those chromatograms may be replaced with another type of chromatogram different from the XIC. For example, it is possible to use a differential chromatogram obtained by computing the difference between the XICs of a plurality of mass-to-charge ratios, or an addition chromatogram obtained by adding the XICs of a plurality of mass-to-charge ratios or by adding all the XICs over a predetermined range of mass-to-charge ratio. For example, in the case of FIG. 4C, the data showing the two XICs obtained at m/z 100 and m/z 101 may be replaced with the data showing one chromatogram obtained by adding the two XICs, i.e. a chromatogram corresponding to m/z=100+101. Such a conversion causes no loss of information in the dimension of mass-to-charge ratio.

In addition to the TIC and XIC, which are the most common chromatograms created by mass spectrometers, there are various forms of chromatograms that can be created. Data which constitute such chromatograms may also be included in the one-dimensional table shown in FIG. 4C. Examples of such chromatograms include a base peak chromatogram, which is a collection of peaks at which the amount of ions is largest, a mass defect chromatogram, an isotopic filtered chromatogram, and a neutral-loss chromatogram. Naturally, it should be understood that some of these chromatograms are based on the data collected by a mass spectrometry of a precursor ion produced by dissociating the ions in the MS unit 3.

The previously described embodiment is an application of the present invention to an LC-MS analyzer system. It is evident that a GC or CE system, which is similarly capable of separating components in the temporal direction, can be used in place of the LC. It is also obvious that various types of analyzing devices other than the mass spectrometer can be used as the analyzer section for acquiring measurement data for samples. For example, in the case where an ultraviolet-visible spectrophotometer is used, it is possible to measure the temporal change of the signal strength for each of a plurality of wavelengths. Accordingly, a chromatogram can be created for each wavelength, and chromatogram data of a plurality of wavelengths obtained for a plurality of samples can be combined into a two-dimensional table by a method similar to the previously described one.

It should be noted that the previously described embodiment is a mere example of the present invention, and any change, modification or addition appropriately made within the spirit of the present invention will naturally fall within the scope of claims of the present patent application.

EXPLANATION OF NUMERALS

1 . . . Sample Changer
2 . . . Liquid Chromatograph (LC) Unit
3 . . . Mass Spectrometer (MS) Unit
4 . . . Controller
5 . . . Operation Unit
6 . . . Display Unit
7 . . . Data Processor
71 . . . Data Collector
72 . . . Chromatogram Creator
73 . . . Data Conversion Processor
74 . . . Multivariate Analysis Processor

The invention claimed is:
1. An analysis data processing method for processing signal-strength data collected for each of a plurality of samples under two or more dimensional separation factors, comprising:
  collecting the signal-strength data by using an analyzing device having: a separator section for separating a plurality of components in a sample along a one-dimensional direction with time serving as the separation factor; and an analyzer section for acquiring, for a sample separated into components by the separator section in the direction of time, a signal strength in a separated form in one or more dimensional directions corresponding to one or more separation factors other than time;

performing automatically a first processing step, in which a process is performed to create a first one-dimensional table in which, while a second variable based on the separation factor in the separator section is sequentially varied under a condition that a first variable based on the separation factor in the analyzer section is fixed, the signal-strength data themselves obtained for respective values of the second variable are arranged in an array direction of the numerical values of the second variable, and this process is repeated, while changing the first variable, to create a plurality of first one-dimensional tables for each of the plurality of samples;

performing automatically a second processing step, in which the plurality of first one-dimensional tables created for the same sample in the first processing step are joined in the array direction of the numerical values of the second variable to create, for each of the plurality of samples, a second one-dimensional table consisting of an array of first one-dimensional tables, which each has a series of signal-strength values associated with a same value of the first variable; and performing automatically a third processing step, in which the second one-dimensional tables respectively created for different samples in the second processing step are arranged in a direction orthogonal to a dimension of the one-dimensional tables to create a two-dimensional table.

2. The analysis data processing method according to claim 1, further comprising a multivariate analysis step in which numerical values held in the two-dimensional table created in the third processing step are read and subjected to a multivariate analysis.

3. The analysis data processing method according to claim 2, wherein the analyzer section is a mass spectrometer in which the mass-to-charge ratio serves as a separation factor.

4. The analysis data processing method according to claim 1, wherein the analyzer section is a mass spectrometer in which the mass-to-charge ratio serves as a separation factor.

5. An analysis data processing system for processing signal-strength data collected for each of a plurality of samples under two or more dimensional separation factors, comprising:

collecting the signal-strength data by using an analyzing device having: a separator section for separating a plurality of components in a sample along a one-dimensional direction with time serving as the separation factor; and an analyzer section for acquiring, for a sample separated into components by the separator section in the direction of time, a signal strength in a separated form in one or more dimensional directions corresponding to one or more separation factors other than time;

performing automatically a first processing section, in which a process is performed to create a first one-dimensional table in which, while a second variable based on the separation factor in the separator section is sequentially varied under a condition that a first variable based on the separation factor in the analyzer section is fixed, the signal-strength data themselves obtained for respective values of the second variable are arranged in an array direction of the numerical values of the second variable, and this process is repeated, while changing the first variable, to create a plurality of first one-dimensional tables for each of the plurality of samples;

performing automatically a second processing section, in which the plurality of first one-dimensional tables created for the same sample in the first processing section are joined in the array direction of the numerical values of the second variable to create, for each of the plurality of samples, a second one-dimensional table consisting of an array of first one-dimensional tables, which each has a series of signal-strength values associated with a same value of the first variable; and performing automatically a third processing section, in which the second one-dimensional tables respectively created for different samples in the second processing section are arranged in a direction orthogonal to the dimension of the one-dimensional tables to create a two-dimensional table.

6. The analysis data processing system according to claim 5, further comprising a multivariate analysis section in which numerical values held in the two-dimensional table created in the third processing section are read and subjected to a multivariate analysis.

7. The analysis data processing system according to claim 6, wherein the analyzer section is a mass spectrometer in which the mass-to-charge ratio serves as a separation factor.

8. The analysis data processing system according to claim 5, wherein the analyzer section is a mass spectrometer in which the mass-to-charge ratio serves as a separation factor.

* * * * *